United States Patent [19]

Moffatt

[11] Patent Number: 5,082,966
[45] Date of Patent: Jan. 21, 1992

[54] SULPHINYL COMPOUNDS AND THEIR PREPARATION

[75] Inventor: Frank S. Moffatt, Reading, England

[73] Assignee: Imperial Chemical Industries plc, England

[21] Appl. No.: 582,307

[22] Filed: Sep. 13, 1990

[30] Foreign Application Priority Data

Sep. 20, 1989 [GB] United Kingdom ............... 8921221

[51] Int. Cl.[5] ................ C07C 317/20; C07C 315/02; C07C 231/02; C07C 233/10
[52] U.S. Cl. .................................... 560/11; 562/429; 564/134; 564/162
[58] Field of Search ........................ 560/11; 562/429; 564/134, 162

[56] References Cited

U.S. PATENT DOCUMENTS 4,853,403  8/1989  Shiraishi et al. ................. 514/404
4,965,395 10/1990  Saeki et al. ........................ 560/11

Primary Examiner—José G. Dees
Assistant Examiner—Vera C. Clarke
Attorney, Agent, or Firm—William E. Dickheiser

[57] ABSTRACT

A compound of the formula

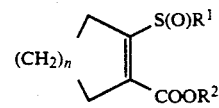

in which $R^1$ is an aralkyl group and $R^2$ is $COOR^2$ hydrogen or a monovalent organic group attached through a carbon atom and preferably is a hydrocarbon group, and n is one or two. Typically $R^2$ is a lower alkyl group. The compound is prepared from the corresponding sulphide compound by oxidation, for example using hydrogen peroxide. The compound can be directly amidated to the corresponding amide which is a precursor for tri- and tetramethyleneisothiazolin-3-ones.

16 Claims, No Drawings

SULPHINYL COMPOUNDS AND THEIR PREPARATION

COMPOUND, PREPARATION AND USE

The present invention relates to a class of new compounds, the preparation thereof and the use of the compounds as intermediates in the production of a class of compounds useful as industrial biocides.

Isothiazolinones are a class of compounds which are known to have useful antimicrobial activity and several compounds of this type are commercially available and are used as industrial biocides, particularly as bactericides.

GB 2087388 discloses a new class of isothiazolinones, specifically of the type 4,5-polymethylene-4-isothiazolin-3-ones. The polymethylene chain contains 3 or 4 carbon atoms or is a chain substituted by a lower alkyl radical having from 1 to 4 carbon atoms. These compounds can be prepared by a process wherein a carbamoylcyclanone is converted to the corresponding carbamoylthiocyclanone which is then cyclised to form the desired isothiazolin-3-one product. The first stage of this procedure uses hydrogen sulphide and gaseous hydrogen chloride and the second stage is carried out in an alcohol solution in the presence of sodium metaperiodate previously fixed to acidic alumina.

GB 2176187 discloses a 2-alkylthio- or 2-aralkylthio-1-cycloalkene-1-carboxamide. According to GB 2176187 the procedure of GB 2087388 is difficult to transfer to the industrial level. The carboxamide compounds of GB 2176187 can be used as intermediate products in the preparation of the isothiazolin-3-one products of GB 2087388. The carboxamide compounds are preferably prepared by the reaction of an alkyl cyclanonecarboxylate in an acidic medium with an alkyl- or aralkylmercaptan, saponifying the ester group to obtain the corresponding 2-alkylthio or 2-aralkylthio carboxylic acid, converting this acid to the acid chloride and then amidating the acid chloride. The thiocarboxamide compound of GB 2176187 is converted to the corresponding sulphoxide by the action of m-chloroperbenzoic acid or the action of hydrogen peroxide in an acidic medium. The sulphoxide can be cyclised to the desired final product (4,5-tri or tetra-methylene-4-isothiazolin-3-one) in a suitable solvent such as methylene chloride in the presence of an acid chloride. The acid chloride specifically disclosed is thionyl chloride, which is used in all of the working examples.

The procedure of GB 2176187 requires many operating stages to prepare the carboxamide intermediate product. Furthermore, the carboxamide intermediate product, and several of the precursors to this intermediate product, contain an alkylthio or aralkylthio group and compounds of this type have an offensive odour, even at parts per billion ($10^9$) concentration levels. Hence, in an industrial process, the procedure of GB 2176187 has the disadvantage of involving many stages and also of requiring containment of the odour in several stages. We have now found that the number of stages can be reduced and the number of stages requiring containment of odours can also be reduced if a new intermediate product is used.

According to the present invention there is provided a sulphinyl cycloalkene carboxylate of the general formula I

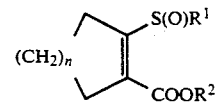

wherein
$R^1$ is an optionally substituted aralkyl group attached to the sulphur atom through an alkyl carbon atom;
$R^2$ is hydrogen or a monovalent organic group attached to the —COO— group through a carbon atom; and
n is one or two.

The groups $R^1$ and $R^2$ may be the same or different and typically will be different. The group $R^2$ is typically an organic group and in particular is an optionally substituted hydrocarbyl group. If either or both of $R^1$ and $R^2$ are substituted groups, the substituents are groups which do not appreciably modify the characteristics of the hydrocarbyl groups and are typically halogen, halohydrocarbyl, nitro, hydrocarbyloxy or hydrocarbylthio. Typically the groups $R^1$ and $R^2$ are unsubstituted or are substituted with halogen or haloalkyl groups such as trifluoromethyl groups. The group $R^1$ is conveniently an unsubstituted aralkyl group and typically contains 7 to 15 carbon atoms. In the group $R^1$ there are at least two hydrogen atoms attached to the carbon atoms in the alpha position relative to the cycloalkene ring. The group $R^2$ may be an alkyl group, an aryl group or an aralkyl group. $R^2$ may contain up to 20 carbon atoms. We have obtained useful results using a compound of formula I in which $R^1$ is an unsubstituted aralkyl group, particularly a benzyl group, and $R^2$ is a lower alkyl group, that is an alkyl group containing not more than six carbon atoms, particularly a methyl group.

The value of n can be one or two and in preferred compounds, which can be used as intermediates in the preparation of trimethylene-4-isothiazolin-3-ones, the value of n is one.

A preferred compound in accordance with the present invention is methyl-(2-benzylsulphinyl)-1-cyclopentene-1-carboxylate, that is a compound of formula I in which $R^1$ is benzyl, $R^2$ is methyl and n is one.

Compounds of formula I can be prepared by the oxidation of the corresponding thio cycloalkene carboxylate. Any suitable oxidation conditions may be used to effect oxidation. Oxidation may be effected using a range of oxidising agents, for example peroxy compounds such as hydrogen peroxide, perbenzoic acid, 3-chloroperbenzoic acid and sodium perborate. We have found that oxidation is conveniently effected using hydrogen peroxide. The oxidation may be effected at a slightly elevated temperature, for example a temperature of not more than 100° C. and preferably not more than 80° C. A temperature of 60° C. to 70° C. is generally satisfactory. The reaction may be effected in acid, neutral or alkaline solution but, as discussed in more detail hereafter, it is convenient to effect the oxidation in an acid solution. Any suitable concentration of hydrogen peroxide can be used, for example 20 to 80% by weight aqueous solution of hydrogen peroxide, and we have obtained satisfactory results using 40% to 60% hydrogen peroxide solutions.

The thio cycloalkene carboxylate can be prepared by the reaction of a suitable thiol compound with a cycloalkanone carboxylate, the procedure being essentially as described in GB 2176187. More specifically, a cycloalkanone carboxylate in an acidic medium is reacted with a thiol compound. The thiol compound is preferably one containing two hydrogen atoms in the alpha position relative to the thiol group. Aralkyl thiol compounds are used and it is generally convenient to use benzylmercaptan.

We have found that the thio cycloalkene carboxylate is susceptible to acid catalysed hydrolysis and this is not desired. To minimise the possibility of any hydrolysis, the reaction product mixture is treated with a base in an amount sufficient to neutralise essentially all of any strong mineral acid which is present. It will be appreciated that the thio cycloalkene carboxylate is a compound containing an aralkyl thio group and compounds of this type generally have an odour which must be contained. To simplify the problems associated with the handling of such a compound, it is desirable to avoid isolating the thio cycloalkene carboxylate. We have found that it is not necessary to isolate the thio cycloalkene carboxylate from the medium in which it is prepared and that this mixture can be oxidised to form the desired sulphinyl compound without isolating the precursor thio compound. Thus, according to a preferred procedure, the reaction of the cycloalkanone carboxylate with the thiol compound and the subsequent oxidation of the thio cycloalkene carboxylate to the sulphinyl compound of the present invention is carried out in a single vessel without separation of the thio cycloalkene carboxylate.

Thus, the sulphinyl compounds of the present invention are preferably prepared by a) reacting a cycloalkanone carboxylate of the general formula II

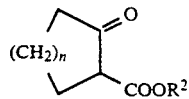

II with a compound R¹SH in an acidic medium; and, without separating the product obtained, b) oxidising the product obtained in a) to obtain a sulphinyl compound of the general formula I, where R¹, R² and n are all as hereinbefore defined.

The acidic medium used in a) may be achieved by passing an acidic gaseous material into the medium which may be, for example, an alkanol or ether. Alternatively, an acid, particularly a carboxylic acid, can be used as a solvent for the reaction but it is generally preferred that there is also present a strong acid which is a mineral acid or an organic sulphonic or phosphoric acid. The acidic compound may be, for example, a mixture of acetic acid and sulphuric acid. The carboxylic acid is used in a sufficient quantity to be effective as a solvent for both the cycloalkanone carboxylate and the thio cycloalkene carboxylate. The strong acid is typically present in an amount of not more than one mole, and generally not more than 0.5 mole, of acid for each mole of the cycloalkanone carboxylate, for example 0.35 mole of a strong acid such as sulphuric acid for each mole of the cycloalkanone carboxylate. The progress of the reaction may be monitored by any suitable means, for example by liquid phase chromatography. When the reaction is complete, a sufficient quantity of a base is added to neutralise all, or essentially all, of the strong acid present. The addition of the base is effected promptly and rapidly once the reaction is complete in order to minimise the possibility of acid hydrolysis. The reaction of a) is conveniently effected without heating and we have found that cooling may be required to maintain the desired reaction temperature which is conveniently close to ambient temperature, for example not more than 40° C., and generally is in the range 15° to 30° C. The addition of base is effected at a temperature which conveniently does not appreciably exceed ambient temperature and it may be necessary to cool the mixture at this stage to avoid undesirably high temperatures.

The oxidation step of b) is effected in the acid medium from a) after treatment with base. The temperature used for the oxidation step is dependent, in particular, on the nature and amount of the oxidising agent. Any suitable oxidising agent can be used and we have obtained useful results using hydrogen peroxide. As noted previously herein, the oxidation may be effected at a temperature which is conveniently in the range 60° to 70° C. However, higher or lower temperatures may be used as desired or necessary.

When the oxidation step is complete, the reaction mixture is cooled, if necessary, to ambient temperature and the desired sulphinyl compound can be isolated by adding the product mixture to an excess of water. To obtain the sulphinyl compound in a useful physical form it has been found to be beneficial to add previously obtained seed crystals of the sulphinyl compound at this stage. Desirably, the suspension of the product crystals is neutralised by the addition of sufficient base to react with the acid, typically acetic acid and possibly sulphuric acid, used in step a) in order to minimise the solubility of the sulphinyl compound in the liquid medium. The solid product is recovered from the suspension thereof by any suitable means, for example by filtration and may be washed with water to remove impurities or may be recrystallised from a suitable solvent which may be, for example, a hydrocarbon, an alcohol or an ester such as toluene, hexane, cyclohexane, methanol, ethanol and ethyl acetate. The product may be dried in a vacuum oven or hot air oven, but drying should be effected at a temperature below the melting point of the product. Since sulphinyl compounds in accordance with the present invention may have melting points of 80° C. or lower, drying is typically effected at a temperature of not more than about 50° C. Conveniently the separated sulphinyl compound is dissolved in a hydrocarbon solvent such as toluene or xylene, the solution obtained is washed with water and may then be used in an amination step as described in more detail hereafter.

The procedure of effecting steps a) and b) in succession without isolating the thio cycloalkene carboxylate means that handling of the thio compound is minimised and the odour of this compound is contained in the vessel in which it is prepared and subsequently converted to the sulphinyl compound. The sulphinyl compound is essentially free from the odours associated with the thio compound and can be handled without the need to contain the odour thereof.

The cycloalkanone carboxylate of the general formula II may be obtained from a diacid or the diester thereof. The diacid may be hexanedioic acid or heptanedioic acid or, more preferably a diester thereof such as the dimethyl ester. The diacid or diester is heated with a base, typically in a hydrocarbon solvent. More specifically a diester is reheated at reflux with sodium methoxide in toluene and methanol is distilled off. A slurry of the sodium salt of the keto ester (the cycloalkanone carboxylate) is obtained which is added to an aqueous acid to produce the cycloalkanone carboxylate in solution in the hydrocarbon solvent. Two phases are produced which can be separated and the toluene is removed from the cycloalkanone carboxylate by distillation.

The sulphinyl compounds of the present invention are readily obtained and can be reacted with an amine to form the sulphoxide of the carboxamide compound of GB 2176187. As is disclosed in GB 2176187, the sulphinyl carboxamide can be cyclised to form a 4,5-tri- or -tetramethylene-4-isothiazolin-3-one. Hence the sulphinyl cycloalkene carboxylate is a useful intermediate in the preparation of cycloalkene isothiazolin-3-ones.

Thus, as a further aspect of the present invention there is provided a process for the preparation of a sulphinyl carboxamide which comprises reacting a sulphinyl cycloalkene carboxylate of the general formula I with an amine of the formula $R^3NH_2$ wherein $R^3$ is hydrogen or a hydrocarbyl group.

The reaction of the carboxylate with the amine may be effected under mild conditions depending on the particular amine. The amine may be one in which $R^3$ is hydrogen, that is the amine is ammonia, and the final isothiazolin-3-one product will be a compound such as 4,5-trimethylene-4-isothiazolin-3-one. If it is desired to obtain an isothiazolin-3-one having a substituent on the nitrogen atom, then the amine used should be one in which the group $R^3$ is a hydrocarbyl group. The group $R^3$ may be an alkyl, cycloalkyl, alkenyl, aryl, aralkyl or alkaryl group and typically contains up to 20 carbon atoms, and especially 1 to 12 carbon atoms. It is generally preferred that $R^3$ is an alkyl group and in particular is a lower alkyl group, as herein defined, for example a methyl group.

The reaction of the carboxylate with the amine is effected in a suitable solvent which may be water if the amine is a lower alkyl amine such as methylamine. Using amines in which the group $R^3$ is a higher alkyl group, the use of other solvents may be necessary, such alternative solvents being hydrocarbon solvents such as hexane, toluene, xylene and petroleum ether or mixtures thereof. The use of water immiscible solvents is generally preferred in order to ease the separation of the aminated product from the unreacted amine.

The reaction between the carboxylate and the amine occurs readily and when using lower alkyl amines a reaction temperature which is close to ambient temperature is satisfactory. More specifically the reaction temperature generally does not exceed 50° C. and preferably is not more than 40° C., for example 25° to 30° C.

The carboxylate is conveniently added to a solution of the amine, for example an aqueous solution. The concentration of amine may be in the range from 10% by weight up to essentially 100% by weight although this is undesirable with lower alkyl amines which have low boiling points and hence are readily volatilised even at ambient temperature and below. The amine concentration is conveniently in the range from 20% by weight up to 60% by weight, for example 40% by weight.

The amine is preferably used in a molar excess relative to the carboxylate. Typically at least 2 moles of amine are used for each mole of the carboxylate and up to 20 moles of amine may be used but no advantages are believed to be attained by the use of greater proportions of the amine. We have obtained satisfactory results using ten moles methylamine for each mole of the carboxylate.

The process of the reaction may be monitored by appropriate analytical techniques, for example by liquid phase chromatography. Under the conditions set out herein, we have found that reaction is typically complete in about six hours.

The reaction product is an amide which forms a precipitate when the reaction is effected in water. The excess, unreacted, amine can be removed from the reaction mixture by distillation under reduced pressure, for example at a pressure of 50 mm of mercury or less which can be achieved using a water pump.

The amide reaction product can be recovered from the reaction mixture by any suitable means such as by filtration. The solid may be washed and dried if desired.

As noted previously herein, the amide may be used to prepare a polymethylene isothiazolin-3-one using a cyclisation step as described in GB 2176187.

Using a compound of formula I in accordance with the present invention, it is possible to prepare a polymethylene isothiazolin-3-one of the type described in GB 2087388 using a process which requires fewer stages than the process of GB 2176187 and which minimises the problems of containment of the odours of the intermediate thio carboxylate compound.

Further aspects of the various features of the present invention are described in more detail hereafter in the following illustrative examples.

EXAMPLE 1 a) Preparation of methylcyclopentanone-2-carboxylate

The preparation was effected in a vertical sided, dish bottomed glass vessel having a capacity of 700 cm$^3$ and provided with a close fitting anchor agitator with blades extending up the vessel walls to the level of the contents of the vessel. 87 g (0.5 mole) of dimethyladipate were charged to a mixture of 90.9 g of a solution of sodium methoxide in methanol containing 29.7% by weight sodium methoxide (=0.5 mole sodium methoxide) and 220 g of toluene with agitation (600 rpm) under a nitrogen blanket.

The mixture was heated to distil off methanol until a batch temperature of 92° C. had been reached and the weight of distillate was 184.3 g. During the distillation, a further 185 g of toluene was charged to replace the distillate and to maintain batch mobility. The distillation and reaction took approximately two hours. The reaction was checked for completion by gas chromatographic analysis.

On completion the reaction mixture was cooled to 30° C. and run into a mixture of 52.8 g of 36% hydrochloric acid (containing 19 g of hydrogen chloride) and 65 g of water over 20 minutes at 15°-25° C. The mixture was agitated for a further 20 minutes when the mixture thinned out considerably.

The mixture was then allowed to separate. The lower aqueous layer was run off and discarded. The upper organic phase was distilled to remove toluene. The crude methylcyclopentanone-2-carboxylate was carried forward for stage b).

b) Preparation of methyl (2-benzylsulphinyl)-1-cyclopentene-1-carboxylate 128 g of glacial acetic acid were agitated at 20°-25° C. and with external cooling. 35 g of 98% sulphuric acid were charged followed by 157.8 g of 90% strength methylcyclopentanone-2-carboxylate (prepared as described in stage a) containing 16 g of toluene, and finally there were added, over a period of 30 minutes, 124 g of benzylmercaptan.

The reaction was tested for completion by liquid phase chromatography analysis and was complete within 60 minutes of the benzylmercaptan charge being completed.

Without any further delay, 59.6 g of 47% aqueous sodium hydroxide (0.7 moles) were charged as quickly as possible whilst maintaining the temperature below 25° C. by external cooling. A mercaptoester solution in acetic acid with suspended sodium sulphate was obtained. This mixture was then heated to 60° C. and 88.4 g of 50% by weight hydrogen peroxide were charged over four hours at 60°-65° C. The reaction was stirred for a further 4 to 6 hours when oxidation was complete as judged by liquid phase chromatography analysis (mercaptoester peak less than 0.75% peak area).

The reaction mixture was cooled to 25° C. before it was charged to 550 cm³ of water with agitation over 40 minutes maintaining the temperature at 20°-25° C. Seed crystals of previously prepared product were charged when approximately 5% of the liquid mixture had been drowned out to induce crystallisation.

The resulting suspension was then neutralised to pH 7-8 by charging 183.3 g of 47% aqueous sodium hydroxide over one hour at 20°-25° C. The suspension was agitated for a further 30 minutes maintaining the pH at 7-8 by the addition of further sodium hydroxide solution as necessary.

The suspension was filtered and the product washed three times on the filter with 250 cm³ of water for each wash before pulling as dry as possible. The paste was then discharged to trays and dried in an oven at 50° C. for 24 hours.

The product had a melting point of 82.1°-82.7° C. after being re-crystallised from toluene twice. By analysis, the product was found to contain C 63.6% wt; H 6.3% wt and S 11.9% wt.

Theory for methyl (2-benzylsulphinyl)-1-cyclopentene-1-carboxylate ($C_{14}H_{16}O_3S$) is C 63.6% wt; H 6.1% wt and S 12.1% wt. The infra red spectrum, the mass spectrum, and the proton and $C^{13}$ n.m.r. spectra were all consistent with the product being methyl (2-benzylsulphinyl)-1-cyclopentene-1-carboxylate.

EXAMPLE 2

Amination of methyl (2-benzylsulphinyl)-1-cyclopentene-1-carboxylate 705 g of 40% by weight solution of methylamine in water were agitated at 20° to 25° C. 263 g of 92% ester sulphoxide (prepared as described in Example 1) were charged as rapidly as possible. The mixture was agitated at 25° to 30° C. until reaction was complete as judged by liquid phase chromatography analysis of a reaction sample. External cooling was used as necessary to control the initial reaction exotherm. A transitory solution was formed before the product precipitated. The reaction was complete within 6 hours.

The temperature of the slurry was raised to 40° C. and a water vacuum (20 mm) gradually applied to distil off excess methylamine. Distillation was continued for 3 hours when equilibrium had been reached. The slurry was cooled to 20° to 25° C. before the product was filtered off. The filter cake was washed five times with water using 50 cm³ for each wash. The solid was then oven dried at 70° to 75° C. to reduce the water content to below 0.5% by weight.

The product obtained was N-methyl-2-benzylsulphinyl-1-cyclopentene-1-carboxamide.

The product of Example 2 may be converted into 2-methyl-4,5-trimethylene-4-isothiazolin-3-one using the procedures disclosed in GB 2176187.

I claim:

1. A sulphinyl cycloalkene carboxylate of the formula I

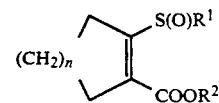

wherein $R^1$ is an aralkyl group containing from 7 to 15 carbon atoms attached to the sulphur atom through an alkyl carbon atom or an aralkyl group containing from 7 to 15 carbon atoms which is substituted by halogen, halohydrocarbyl, nitro, hydrocarbyloxy or hydrocarbylthio;

$R^2$ is hydrogen or an alkyl, aryl or aralkyl group containing up to 20 carbon atoms; and n is one or two.

2. The compound of claim 1 wherein $R^2$ is a lower alkyl containing not more than six carbon atoms.

3. The compound of claim 1 wherein $R^1$ is benzyl or benzyl substituted by halogen, halohydrocarbyl, nitro, hydrocarbyloxy or hydrocarbylthio and $R^2$ is a lower alkyl group.

4. The compound of claim 1 wherein $R^1$ is benzyl or benzyl substituted by halogen, halohydrocarbyl, nitro, hydrocarbyloxy or hydrocarbylthio.

5. Methyl-(2-benzylsulphinyl)-1-cyclopentene-1-carboxylate.

6. A process for the preparation of a compound of the formula I

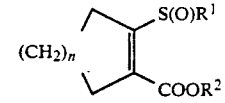

which comprises oxidizing a thio cycloalkane carboxylate of the formula III

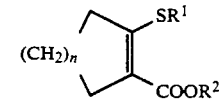

wherein $R^1$ is an aralkyl group containing from 7 to 15 carbon atoms attached to the sulphur atom through an alkyl carbon atom or an aralkyl group containing from 7 to 15 carbon atoms which is substituted by halogen halohydrocarbyl, nitro, hydrocarbyloxy or hydrocarbylthio;

$R^2$ is hydrogen or an alkyl, aryl or aralkyl group containing up to 20 carbon atoms; and n is one or two.

7. The process of claim 6 wherein the compound of the formula III is oxidized in acid solution using hydrogen peroxide.

8. The process of claim 6 where the oxidation is effected at a temperature of not more than 100° C.

9. The process of claim 6 wherein the compound of the formula III has been obtained by the reaction of a cycloalkanone carboxylate of the formula II

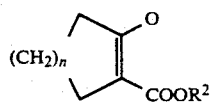

with a compound $R^1SH$ in an acidic medium and, without separating the product, effecting the oxidation to obtain the sulphinyl product, where $R^1$, $R^2$ and n are all as defined.

10. The process of claim 9 wherein the acidic medium contains a strong acid and, on completion of the reaction with $R^1SH$, a sufficient quantity of a base is added to neutralise the strong acid present.

11. The process of claim 10 wherein the acidic medium is a carboxylic acid which is a solvent for the reaction and which contains the strong acid.

12. The process of claim 6 wherein $R^1$ is a benzyl group, $R^2$ is a lower alkyl group and n has a value of one.

13. The process of claim 12 wherein $R^2$ is a methyl group.

14. A process for the preparation of a sulphinyl carboxamide wherein a compound of the formula I

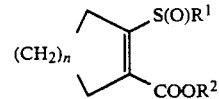

is reacted with an amine of the formula $R^3NH_2$ wherein
$R^1$ is an aralkyl group containing from 7 to 15 carbon atoms attached to the sulphur atom through an alkyl carbon atom or an aralkyl group containing from 7 to 15 carbon atoms which is substituted by halogen halohydrocarbyl, nitro, hydrocarbyloxy or hydrocarbylthio;
$R^2$ is hydrogen or an alkyl, aryl or aralkyl group containing up to 20 carbon atoms; and
$R^3$ is hydrogen or hydrocarbyl containing up to 20 carbon atoms and is selected from an alkyl, cycloalkyl, alkenyl, aryl, aralkyl or alkaryl group; and
n is one or two.

15. The process of claim 14 wherein $R^3$ is a lower alkyl group containing not more than six carbon atoms.

16. The process of claim 15 wherein the reaction is effected in an aqueous solution of the amine.

* * * * *